(12) United States Patent
Lalleman

(10) Patent No.: US 7,713,310 B2
(45) Date of Patent: *May 11, 2010

(54) DYEING PROCESS COMPRISING A ZINC-BASED COMPOUND FOR WASH-PROTECTING THE COLOR OF ARTIFICIALLY DYED KERATIN FIBERS

(75) Inventor: Boris Lalleman, Paris (FR)

(73) Assignee: L'Oreal S.A., Paris (FR)

(*) Notice: Subject to any disclaimer, the term of this patent is extended or adjusted under 35 U.S.C. 154(b) by 36 days.

This patent is subject to a terminal disclaimer.

(21) Appl. No.: 11/976,643

(22) Filed: Oct. 26, 2007

(65) Prior Publication Data

US 2008/0134449 A1 Jun. 12, 2008

Related U.S. Application Data

(60) Provisional application No. 60/856,012, filed on Nov. 2, 2006.

(30) Foreign Application Priority Data

Oct. 26, 2006 (FR) .................................. 06 54563

(51) Int. Cl.
*A61Q 5/10* (2006.01)
*A61Q 5/00* (2006.01)

(52) U.S. Cl. ................ 8/405; 8/406; 8/435; 8/629; 424/70.1; 132/202; 132/208

(58) Field of Classification Search ......... 8/405, 8/406, 435, 629; 424/70.13, 70.1; 132/202, 132/208
See application file for complete search history.

(56) References Cited

U.S. PATENT DOCUMENTS

| | | | |
|---|---|---|---|
| 3,445,566 A | 5/1969 | Skoultchi et al. | |
| 4,173,453 A | 11/1979 | Shiah | |
| 4,652,445 A | 3/1987 | Ort | |
| 5,609,650 A | 3/1997 | Knuebel et al. | |
| 5,635,168 A * | 6/1997 | Burns et al. | 424/70.4 |
| 6,008,359 A | 12/1999 | Jachowicz et al. | |
| 6,723,136 B2 | 4/2004 | Pruche | |
| 6,953,486 B2 | 10/2005 | Pruche | |
| 7,153,330 B2 | 12/2006 | Cotteret | |
| 7,270,685 B2 | 9/2007 | Dreher et al. | |
| 2004/0060126 A1* | 4/2004 | Cottard et al. | 8/405 |
| 2004/0148712 A1 | 8/2004 | Pruche et al. | |
| 2005/0089483 A1 | 4/2005 | Chun et al. | |
| 2005/0255069 A1* | 11/2005 | Muller | 424/70.13 |
| 2006/0182697 A1 | 8/2006 | Lalleman et al. | |

FOREIGN PATENT DOCUMENTS

| | | |
|---|---|---|
| CA | 2063062 | 10/1992 |
| DE | 1 958 336 | 3/1972 |
| DE | 42 08 297 | 9/1993 |
| DE | 100 51 773 | 4/2002 |
| EP | 0 335 403 | 10/1989 |
| EP | 1 210 931 | 6/2002 |
| EP | 1 424 060 | 6/2004 |
| EP | 1688127 | 8/2006 |
| FR | 2 722 685 | 1/1996 |
| FR | 2 814 943 | 4/2002 |
| FR | 2 838 053 | 10/2003 |
| FR | 2 880 801 | 7/2006 |
| JP | 2003 95897 | 4/2003 |
| WO | WO 96/09030 | 3/1996 |
| WO | WO 02/051371 | 7/2002 |

OTHER PUBLICATIONS

French Search Report for French Application No. 0654563 dated Jun. 15, 2007.
English language Abstract of DE 100 51 773, dated Apr. 25, 2002.
English language Abstract of FR 2 722 685, dated Jan. 16, 1996.
English language Abstract of JP 2003-95897, dated Apr. 3, 2003.
Copending U.S. Appl. No. 11/976,642, filed Oct. 26, 2007.
European Search Report for EP 07 11 8232, dated Feb. 26, 2008.
French Search Report for FR 06/54562, dated Jun. 26, 2007.
Office Action dated Oct. 15, 2009 for copending U.S. Appl. No. 11/976,642.

* cited by examiner

*Primary Examiner*—Eisa B Elhilo
(74) *Attorney, Agent, or Firm*—Finnegan, Henderson, Farabow, Garrett & Dunner LLP

(57) ABSTRACT

The present disclosure relates to a cosmetic process for wash-protecting the color of keratin fibers comprising applying a composition comprising, in a cosmetically acceptable medium, at least one zinc-based compound chosen from zinc-based mineral compounds and zinc-based non-nitrogenous organic compounds to keratin fibers previously dyed. Also disclosed is a cosmetic process for wash-protecting the color of dyed keratin fibers, comprising applying to the keratin fibers, after dyeing, at least one zinc-based compound chosen from zinc-based mineral compounds and zinc-based non-nitrogenous organic compounds. The present disclosure further relates to a process for dyeing keratin fibers comprising applying to the fibers at least one dye composition (A), optionally in the presence of an oxidizing agent, for period of time that is sufficient to develop the color, and applying a composition (B) comprising, in a cosmetically acceptable medium, at least one zinc-based compound as defined herein.

22 Claims, No Drawings

DYEING PROCESS COMPRISING A ZINC-BASED COMPOUND FOR WASH-PROTECTING THE COLOR OF ARTIFICIALLY DYED KERATIN FIBERS

This application claims benefit of U.S. Provisional Application No. 60/856,012, filed Nov. 2, 2006, the contents of which are incorporated herein by reference. This application also claims benefit of priority under 35 U.S.C. § 119 to French Patent Application No. 0654563, filed Oct. 26, 2006, the contents of which are also incorporated herein by reference.

Disclosed herein is a process for wash-protecting the color of keratin fibers, for example, human keratin fibers, such as human hair, comprising applying a composition comprising at least one zinc-based compound chosen from zinc-based mineral compounds and zinc-based non-nitrogenous organic compounds on keratin fibers dyed beforehand by direct dyeing or by oxidation dyeing in the presence of an oxidizing agent.

It is known practice to dye keratin fibers, for example, human keratin fibers such as the hair, with dye compositions comprising oxidation dye precursors, which are generally known as oxidation bases. These oxidation bases are colorless or weakly colored compounds, which, when combined with oxidizing products, give rise to colored compounds via a process of oxidative condensation. It is also known that the shades obtained with these oxidation bases can be varied by combining them with couplers or coloration modifiers. The variety of molecules used as oxidation bases and couplers allows a wide range of colors to be obtained.

It is also known practice to dye keratin fibers by direct dyeing. The process conventionally used in direct dyeing comprises applying to the keratin fibers direct dyes, which are colored and coloring molecules that have affinity for the fibers, leaving them to act, and then rinsing the fibers.

The colorations resulting there from can be for instance, chromatic colorations, but are, however, temporary or semi-permanent. It is believed that the nature of the interactions that bind the direct dyes to the keratin fiber and their desorption from the surface and/or core of the fiber are responsible for their semi-permanent dyeing power and weak wash-fastness.

The artificial color of hair provided by a direct or oxidation dyeing treatment gradually attenuates as a result of repeated washing and leads to fading of the coloration of the hair over time. Furthermore, the use of commercial rinse-out and leave-in care products does not sufficiently improve the fastness of the artificial color of hair.

There is thus a need in the art to develop methods for protecting the artificial color from the effect of repeated washing.

Organic mineral zinc salts are generally known in hair dyeing as catalysts for oxidation dyeing with atmospheric oxygen using specific oxidation dye precursors. In European Patent No. 0 335 403, zinc salts are used for the mild oxidation dyeing of hair with tannins, for instance, catechin or tannic acid. In French Patent No. 2 814 943 and European Patent Application Nos. 1 424 060 and 1 210 931, zinc salts are used in a catalytic system also comprising hydrogen carbonates to develop the color of oxidation dye precursors of the ortho-diphenol type. German Patent No. 4 209 897 and French Patent No. 2 722 685 also describe oxidation dyeing processes based on indole or indoline compounds and zinc salts.

Japanese Patent Application No. 2003-095 897 discloses treating compositions for preventing perturbation of the shade of bleached hair caused by light, shampooing at the time of dyeing or the use of peroxide. These compositions contain a hydroxycarboxylic acid, chosen, for example, copper gluconate, zinc gluconate and 2-glucoside gallic acid.

The present inventors have discovered, surprisingly, that the use of at least one-based compound chosen from zinc-based mineral compounds and zinc-based non-nitrogenous organic compounds affords wash-protection of the artificial color of keratin fibers dyed by direct dyeing or by oxidation dyeing in the presence of an oxidizing agent.

The various embodiments of the present disclosure are described in more detail below. All meanings and definitions provided herein with respect to the compounds used in the present disclosure are applicable to all embodiments of the present disclosure.

As used herein, "oxidizing agent" is understood to mean any compound having oxidizing properties and being other than atmospheric oxygen.

As used herein, "zinc-based mineral compound" is understood to mean any inorganic compound comprising in its structure at least one zinc atom.

As used herein, "zinc-based non-nitrogenous organic compound" is understood to mean any organic compound comprising in its structure at least one zinc atom and not comprising any nitrogen atoms.

As used herein, "human keratin fibers" is understood to mean head hair, body hair, for example, the beard, moustache, eyelashes and the eyebrows.

As used herein, "artificially dyed keratin fibers" is understood to mean keratin fibers dyed either via a direct dyeing process or via an oxidation dyeing process.

As disclosed herein, "washing" is understood to mean at least one application on the keratin fibers of an aqueous rinse-out composition, which is usually a detergent composition such as a shampoo. It is also understood to mean bathing or swimming, for example, in the sea or in a swimming pool.

Disclosed herein is thus a process for wash-protecting the color of artificially dyed keratin fibers, comprising applying to the fibers, after dyeing the fibers, at least one zinc-based compound chosen from zinc-based mineral compounds and zinc-based non-nitrogenous organic compounds or a composition comprising, in a cosmetically acceptable medium, at least one zinc-based compound chosen from zinc-based mineral compounds and zinc-based non-nitrogenous organic compounds.

Furthermore, the protection afforded by the treatment as disclosed herein is long-lasting and does not require frequent reapplication of the product.

Also disclosed herein is a dyeing process that comprises applying to keratin fibers, for example, human keratin fibers such as the hair, at least one dye composition (A) chosen from direct dye compositions and oxidation dye compositions, optionally in the presence of at least one oxidizing agent, for a period of time that is sufficient to develop the color, and in following this application by applying a composition (B) comprising, in a cosmetically acceptable medium, at least one zinc-based compound chosen from zinc-based mineral compounds and zinc-based non-nitrogenous organic compounds.

According to at least one embodiment, the at least one zinc-based compound is chosen from water-soluble zinc salts.

As used herein "water-soluble zinc salt" is understood to mean any salt which, after having been fully dissolved with stirring at 1% in an aqueous solution at a temperature of 25° C., gives a solution comprising an amount of insoluble salt of less than 0.05% by weight.

The at least one water-soluble zinc salt may, in at least one embodiment, be chosen from zinc sulfate, zinc chloride, zinc lactate, zinc gluconate, zinc phenolsulfonate, zinc salicylate, and derivatives thereof.

According to at least on embodiment, zinc salicylate and derivatives thereof can be chosen from those of formula (I):

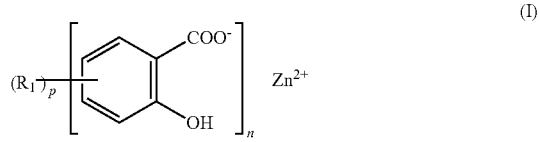

wherein:

n is 2;

p is chosen from 0, 1, 2 and 3;

$R_1$ is chosen from linear and branched $C_1$-$C_{18}$ alkyl radicals, for example, methyl, ethyl, n-propyl, isopropyl or n-butyl; linear and branched $C_1$-$C_{18}$ hydroxyalkyl radicals; halogen atoms, for example iodine, bromine or chlorine; $C_2$-$C_{18}$ acyl radicals, for example acetyl; and $COR_2$, $OCOR_2$ and $CONHR_2$ radicals wherein $R_2$ is chosen from a hydrogen atom and linear and branched $C_1$-$C_{18}$ alkyl radicals.

A non-limiting example of a water-soluble zinc salt that may be used herein is zinc gluconate, for instance, the commercial product sold under the name Givobio G Zn by the company SEPPIC.

The cosmetically acceptable medium for the color-protecting compositions according to the present disclosure may comprise, for example, water or a mixture of water and at least one cosmetically acceptable organic solvent. Non-limiting examples of organic solvents may include $C_1$-$C_4$ lower alkanols, such as ethanol and isopropanol; polyols and polyol ethers, for instance, 2-butoxyethanol, propylene glycol, propylene glycol monomethyl ether and diethylene glycol monomethyl ether and monoethyl ether, and mixtures thereof.

According to the present disclosure, the at least one zinc-based compound may be present in the color-protecting composition in an amount ranging from 0.005% to 30% by weight, for example, from 0.1% to 20% by weight and further for example, from 0.3% to 15% by weight relative to the total weight of the composition.

The at least one solvent which may be used in at least one embodiment of the present disclosure may be present in an amount ranging from 1% to 40% by weight, for example, ranging from 3% to 10% by weight relative to the total weight of the composition.

The composition disclosed herein may also contain at least one adjuvant conventionally used in hair-treating compositions. Useful adjuvants may include: anionic, cationic, non-ionic, amphoteric, zwitterionic surfactants and mixtures thereof, anionic, cationic, nonionic, amphoteric, zwitterionic polymers and mixtures thereof, mineral and organic thickeners, for example, anionic, cationic, nonionic and amphoteric polymeric associative thickeners, penetrants, sequestrants, fragrances, buffers, dispersants, conditioning agents, for instance, volatile and non-volatile, modified and unmodified silicones, film-forming agents, ceramides, preserving agents and opacifiers.

The composition disclosed herein may also contain at least one conditioning agent.

As used herein, "conditioning agent" is understood to mean any agent whose function is to improve the cosmetic properties of the hair, for example, the softness, disentangling, feel, smoothness and static electricity.

The at least one conditioning agent that may be used in the present disclosure may be in liquid, semi-solid or solid form, for example, oils, waxes and gums.

Other useful non-limiting examples of the at least one conditioning agent may include synthetic oils such as polyolefins, plant oils, fluoro oils, perfluoro oils, natural and synthetic waxes, silicones, non-polysaccharide cationic polymers, compounds of ceramide type, cationic surfactants, fatty amines, saturated fatty acids and esters of fatty acids other than those of the disclosure, and mixtures thereof.

The synthetic oils that may be used in the present disclosure may, in at least one embodiment, be chosen from polyolefins, for example, poly-α-olefins and further for example, hydrogenated or non-hydrogenated polybutene type, for instance, hydrogenated or non-hydrogenated polyisobutene type.

In at least one embodiment, isobutylene oligomers of molecular weight less than 1000 and mixtures thereof with polyisobutylenes of molecular weight greater than 1000, for example, ranging from 1000 to 15,000 are used.

Examples of poly-α-olefins include, but are not limited to those sold, for instance, under the name Permethyl 99 A, 101 A, 102 A, 104 A (n=16) and 106 A (n=38) by the company Presperse Inc., or alternatively the products sold, for example, under the name Arlamol HD (n=3) by the company ICI (n denoting the degree of polymerization), of hydrogenated or non-hydrogenated polydecene type.

Such products are sold, for example, under the names Ethylflo by the company Ethyl Corp. and Arlamol PAO by the company ICI.

The animal or plant oils which may be used in at least one embodiment of the present disclosure may be chosen from, by way of non-limiting example, sunflower oil, corn oil, soybean oil, avocado oil, jojoba oil, marrow oil, grapeseed oil, sesame oil, hazelnut oil, fish oils, glyceryl tricaprocaprylate, and plant or animal oils of formula $R_9COOR_{10}$ wherein $R_9$ is a higher fatty acid residue comprising from 7 to 29 carbon atoms and $R_{10}$ is a linear or branched hydrocarbon-based chain comprising from 3 to 30 carbon atoms, for example, alkyl or alkenyl, and further for example, purcellin oil.

Natural or synthetic essential oils such as eucalyptus oil, lavandin oil, lavender oil, vetiver oil, *Litsea cubeba* oil, lemon oil, sandalwood oil, rosemary oil, camomile oil, savory oil, nutmeg oil, cinnamon oil, hyssop oil, caraway oil, orange oil, geraniol oil, cade oil and bergamot oil may also be used.

According to at least one embodiment, the waxes are natural (animal or plant) or synthetic substances that are solid at ambient temperature (20°-25° C.). They are insoluble in water, soluble in oils and are capable of forming a water-repellent film.

For the definition of waxes, reference may be made to the document, P. D. Dorgan, Drug and Cosmetic Industry, December 1983, pp. 30-33.

The wax or waxes which may be used in the context of the present disclosure may be chosen, by way of non-limiting example, from carnauba wax, candelilla wax, alfalfa wax, paraffin wax, ozokerite, plant waxes such as olive tree wax, rice wax, hydrogenated jojoba wax or the absolute waxes of flowers such as the essential wax of blackcurrant flower sold by the company Bertin (France), animal waxes such as beeswaxes, or modified beeswaxes (cerabellina); other waxes or waxy starting materials which may be used are, for instance, marine waxes such as those sold by the company Sophim under the reference M82, and polyethylene waxes or polyolefin waxes in general.

In at least one embodiment, the conditioning agent may be chosen from cationic polymers and silicones.

Among the non-saccharide cationic polymers that may be used in the context of the present disclosure may be chosen, by way of non-limiting example, from all those already known in the art to improve the cosmetic properties of hair treated with detergent compositions, for instance, those described in European Patent Application No. 0 337 354 and in French Patent Application Nos. 2 270 846, 2 383 660, 2 598 611, 2 470 596 and 2 519 863.

As used herein, "cationic polymer" is understood to mean any polymer comprising cationic groups and/or groups that may be ionized into cationic groups.

Among the cationic polymers that may be used in the present disclosure, non-limiting mention may be made of those which contain primary, secondary, tertiary and/or quaternary amine groups capable of forming part of the main polymer chain or of being borne by a side substituent directly bound to the latter.

In at least one embodiment, cationic polymers that may be used herein, have a number-average molecular mass ranging from 500 to $5 \times 10^6$, for example, ranging from $10^3$ to $3 \times 10^6$.

Suitable cationic polymers may include, by way of non-limiting example, polymers of the polyamine, polyamino amide and polyquaternary ammonium type.

These polymers of the polyamine, polyamino amide and polyquaternary ammonium type that may be used herein, may be chosen, for example, from those described in French Patents Nos. 2 505 348 and 2 542 997. Among these polymers, the following may be cited:

(1) homopolymers or copolymers derived from acrylic or methacrylic esters or amides and comprising at least one unit of the following formulae:

wherein:

$R_3$ and $R_4$, which may be identical or different, are chosen from hydrogen and $C_1$-$C_6$ alkyl groups, for example, methyl or ethyl;

$R_5$, which may be identical or different, is chosen from hydrogen and a $CH_3$ radical;

A, which may be identical or different, is chosen from linear and branched $C_1$-$C_6$ alkyl groups for example, ethyl or propyl or a hydroxy($C_1$-$C_4$)alkyl group;

$R_6$, $R_7$ and $R_8$, which may be identical or different, are chosen from $C_1$-$C_{18}$ alkyl groups and a benzyl radical, for example, $C_1$-$C_6$ alkyl groups;

X is chosen from an anion derived from a mineral or organic acid, such as a methosulfate anion and a halide, such as chloride or bromide.

The copolymers of family (1) can also contain at least one unit derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters. Examples of copolymers of family (1) that are suitable for use in accordance with the present disclosure include, but are not limited to:

copolymers of acrylamide and of dimethylaminoethyl methacrylate quaternized with dimethyl sulfate or with a dimethyl halide, such as those sold, for instance, under the name Hercofloc by the company Hercules, the copolymers of acrylamide and of methacryloyloxyethyltrimethylammonium chloride described, for example, in European Patent Application No. 0 80 976 and sold, for example, under the name Bina Quat P 100 by the company Ciba Geigy, the copolymer of acrylamide and of methacryloyloxyethyltrimethylammonium methosulfate sold, for instance, under the name Reten by the company Hercules, quaternized or non-quaternized vinylpyrrolidone/dialkylaminoalkyl acrylate or methacrylate copolymers, such as the products sold under the name Gafquat by the company ISP, for example, Gafquat 734 or Gafquat 755, or alternatively the products Copolymer 845, 958 and 937. These polymers are described in detail in French Patent Nos. 2 077 143 and 2 393 573, dimethylaminoethyl methacrylate/vinylcaprolactam/vinylpyrrolidone terpolymers, such as the product sold, for instance, under the name Gaffix VC 713 by the company ISP, vinylpyrrolidone/methacrylamidopropyldimethylamine copolymers sold, for example, under the name Styleze CC 10 by ISP, and quaternized vinylpyrrolidone/dimethylaminopropylmethacrylamide copolymers, such as the product sold, for instance, under the name Gafquat HS 100 by the company ISP.

(2) Polymers comprising piperazinyl units and divalent alkylene or hydroxyalkylene radicals comprising straight or branched chains, which may be interrupted by at least one atom chosen from oxygen, sulfur and nitrogen atoms or by aromatic or heterocyclic rings, as well as the oxidation and/or quaternization products of these polymers. These polymers are described in French Patent Nos. 2 162 025 and 2 280 361.

(3) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 mol to 0.35 mol per amine group of the polyamino amide; these polyamino amides can be alkylated or, if they comprise at least one tertiary amine functional group, they can be quaternized. These polymers are described in French Patent Nos. 2 252 840 and 2 368 508.

(4) The polyamino amide derivatives resulting from the condensation of polyalkylene polyamines with polycarboxylic acids followed by alkylation with difunctional agents, for example, adipic acid/dialkylaminohydroxyalkyl-dialkylenetriamine polymers wherein the alkyl radical comprise from 1 to 4 carbon atoms, for example, methyl, ethyl or propyl. These polymers are described in French Patent No. 1 583 363.

Among these derivatives, non-limiting mention may be made, for instance, of the adipic acid/dimethylaminohydroxypropyl/diethylenetriamine polymers sold, for example, under the name Cartaretine F, F4 or F8 by the company Sandoz.

(5) The polymers obtained by reaction of a polyalkylene polyamine comprising two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid ranges from 0.8:1 to 1.4:1; the polyamino amide that results from reaction with epichlorohydrin in a molar ratio of epichlorohydrin relative to the secondary amine group of the polyamino amide ranges from 0.5:1 to 1.8:1. These polymers are described in U.S. Pat. Nos. 3,227,615 and 2,961,347.

Polymers of this type are sold, for example, under the name Hercosett 57 by the company Hercules Inc. or alternatively under the name PD 170 or Delsette 101 by the company Hercules in the case of the adipic acid/epoxypropyl/diethylenetriamine copolymer.

(6) Cyclopolymers of alkyldiallylamine or of dialkyldiallylammonium, such as the homopolymers or copolymers comprising, as main constituent of the chain, units chosen from those of formulae (VII) and (VIII):

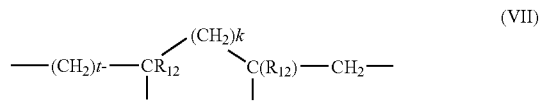

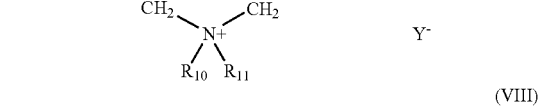

wherein:
k and t are 0 or 1;
the sum of k+t is 1;
$R_{12}$ is chosen from hydrogen and a methyl radical;
$R_{10}$ and $R_{11}$ are chosen from, independently of one another, $C_1$-$C_6$ alkyl groups, hydroxy ($C_1$-$C_5$) alkyl groups and a lower ($C_1$-$C_4$) amidoalkyl group, or $R_{10}$ and $R_{11}$ may form, together with the nitrogen atom to which they are attached, heterocyclic groups such as piperidyl or morpholinyl;
$Y^-$ is chosen from anions such as bromide, chloride, acetate, borate, citrate, tartrate, bisulfate, bisulfite, sulfate and phosphate. These polymers are described in French Patent No. 2 080 759 and in its Certificate of Addition 2 190 406.

According to at least one embodiment of the present disclosure, $R_{10}$ and $R_{11}$, independently of each other, may be chosen from $C_1$-$C_4$ alkyl groups.

Among the polymers defined above, non-limiting mention may be made, for example, of the dimethyldiallylammonium chloride homopolymer sold, for instance, under the name Merquat 100 by the company Nalco (and its homologues of low weight-average molecular mass) and the copolymers of diallyldimethylammonium chloride and of acrylamide, sold, for example, under the name Merquat 550.

(7) The quaternary diammonium polymer comprising repeating units chosen from those of formula:

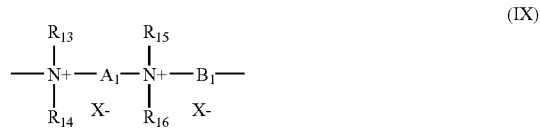

wherein:
$R_{13}$, $R_{14}$, $R_{15}$, and $R_{16}$, which may be identical or different, are chosen from aliphatic, alicyclic, arylaliphatic radicals comprising from 1 to 20 carbon atoms and lower hydroxyalkylaliphatic radicals, or alternatively $R_{13}$, $R_{14}$, $R_{15}$ and $R_{16}$, together or separately, form with the nitrogen atoms to which they are attached, heterocycles optionally comprising a second heteroatom other than nitrogen, or alternatively $R_{13}$, $R_{14}$, $R_{15}$ and $R_{16}$ are chosen from linear and branched $C_1$-$C_6$ alkyl radicals substituted with a nitrile, ester, acyl or amide group or a group —CO—O—$R_{17}$-D or —CO—NH—$R_{17}$-D wherein $R_{17}$ is an alkylene and D is a quaternary ammonium group;

$A_1$ and $B_1$ are chosen from $C_2$-$C_{20}$ polymethylene groups which may be linear or branched, saturated or unsaturated, and which may comprise, linked to or intercalated in the main chain, at least one aromatic ring or at least one oxygen or sulfur atom or sulfoxide, sulfone, disulfide, amino, alkylamino, hydroxyl, quaternary ammonium, ureido, amide or ester groups, and $X^-$ is an anion derived from a mineral or organic acid;

$A_1$, $R_{13}$ and $R_{15}$ can form, with the two nitrogen atoms to which they are attached, a piperazine ring; in addition, if $A_1$ is a linear or branched, saturated or unsaturated alkylene or hydroxyalkylene radical, $B_1$ may comprise a group $(CH_2)_{np}$—CO-D-OC—$(CH_2)_p$—, wherein p is an integer ranging from 2 to 20, wherein D is chosen from:

a) a glycol residue of formula: —O-Z-O—, wherein Z is chosen from linear and branched hydrocarbon-based radicals or a group corresponding to one of the following formulae:

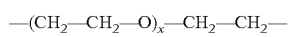

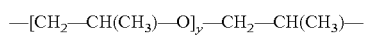

wherein x and y are decimals or integers ranging from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, wherein Y is chosen from linear and branched hydrocarbon-based radicals, or alternatively the divalent radical

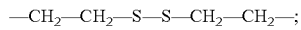

d) a ureylene group of formula: —NH—CO—NH—.

In at least one embodiment, $X^-$ is an anion such as chloride or bromide.

The polymers which may be used in the context of the present disclosure may have a number-average molecular mass ranging from 1000 and 100,000.

These polymers are further described in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

In at least one embodiment, polymers that comprise repeating units corresponding to the formula (a) may be used:

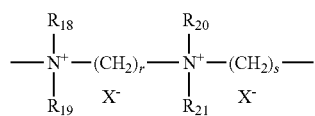

wherein:

$R_{18}$, $R_{19}$, $R_{20}$ and $R_{21}$, which may be identical or different, are chosen from $C_1$-$C_4$ alkyl groups or hydroxy($C_1$-$C_4$)alkyl radicals;

r and s are integers ranging from 2 to 20;

$X^-$ is an anion derived from a mineral or organic acid.

In another embodiment, a compound of formula (a) wherein $R_{18}$, $R_{19}$, $R_{20}$ and $R_{21}$ are methyl radicals and r is 3, s is 6 and X is Cl, referred to as hexadimethrine chloride according to the INCI nomenclature (CTFA) may be used.

(8) Polyquaternary ammonium polymers comprising units of formula (X):

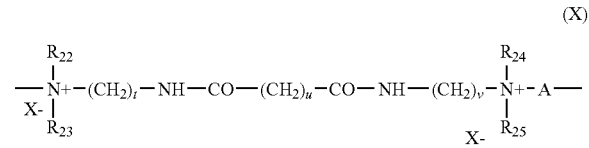

wherein:

$R_{22}$, $R_{23}$, $R_{24}$ and $R_{25}$, which may be identical or different, are chosen from a hydrogen atom, a methyl, ethyl, propyl, β-hydroxyethyl, β-hydroxypropyl and a —$CH_2CH_2$(OCH$_2$CH$_2$)$_p$OH radical, wherein p is 0 or an integer ranging from 1 to 6, with the proviso that $R_{22}$, $R_{23}$, $R_{24}$ and $R_{25}$ are not simultaneously hydrogen, t and u, which may be identical or different, are integers ranging from 1 to 6, v is 0 or an integer ranging from 1 to 34, $X^-$ is an anion, for example, halide, A is chosen from a divalent radical and —$CH_2$—$CH_2$—O—$CH_2$—$CH_2$—.

These compounds are described in European Patent Application No. 122 324.

In at least one embodiment, non-limiting mention may be made, for example, of Mirapol® A 15, Mirapol® AD1, Mirapol® AZ1 and Mirapol® 175 sold by the company Miranol.

(9) Quaternary polymers of vinylpyrrolidone and of vinylimidazole, such as, the products sold under the names Luviquat® FC 905, FC 550 and FC 370 by the company BASF.

(10) Crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, for instance, methylenebisacrylamide. In at least one embodiment, the polymer may be a crosslinked acrylamide/methacryloyloxyethyltrimethylammonium chloride copolymer (20/80 by weight) in the form of a dispersion containing 50% by weight of the said copolymer in mineral oil. This dispersion is sold, for example, under the name Salcare® SC 92 by the company Ciba. In another embodiment, the polymer may be a crosslinked methacryloyloxyethyltrimethylammonium chloride homopolymer comprising about 50% by weight of the homopolymer in mineral oil or in a liquid ester. These dispersions are sold, for instance, under the names Salcare® SC 95 and Salcare® SC 96 by the company Ciba.

(11) Cationic polysaccharides, for example, celluloses and cationic galactomannan gums.

The cationic polysaccharides may, in at least one embodiment, be chosen from cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups, are described in French Patent No. 1 492 597. These polymers are also defined, for instance, in the CTFA dictionary as hydroxyethylcellulose quaternary ammoniums that have reacted with an epoxide substituted with a trimethylammonium group.

The cationic cellulose copolymers or cellulose derivatives grafted with a water-soluble quaternary ammonium monomer are described in U.S. Pat. No. 4,131,576, such as hydroxyalkylcelluloses, for instance hydroxymethyl-, hydroxyethyl- or hydroxy-propylcelluloses grafted, for instance, with a methacryloylethyltrimethylammonium, methacrylamidopropyltrimethylammonium or dimethyldiallylammonium salt.

The cationic galactomannan gums are described in U.S. Pat. Nos. 3,589,578 and 4,031,307, for example, guar gums comprising trialkylammonium cationic groups and guar gums modified with a salt, for instance, chloride of 2,3-epoxypropyl-trimethylammonium.

Also suitable as cationic polymers are cationic proteins or cationic protein hydrolysates, polyalkyleneimines, for example, polyethyleneimines, polymers comprising vinylpyridine or vinylpyridinium units, condensates of polyamines and of epichlorohydrin, quaternary polyureylenes and chitin derivatives.

In at least one embodiment, the cationic polymers are chosen from cationic cyclopolymers, for example, the dimethyldiallylammonium chloride homopolymers or copolymers sold, for instance, under the names Merquat 100, Merquat 550 and Merquat S by the company Nalco, and quaternary vinylpyrrolidone and vinylimidazole polymers, cationic polysaccharides and mixtures thereof.

Suitable silicones that may be used in at least one embodiment of the present disclosure are polyorganosiloxanes that are insoluble in the composition and that may be in the form of oils, waxes, resins or gums.

The organopolysiloxanes are defined, for instance, in Walter Noll's "Chemistry and Technology of Silicones" (1968) Academic Press. They may be volatile or non-volatile.

Non-limiting examples of silicones that may be used in accordance with the present disclosure may include volatile silicones that have a boiling point ranging from 60° C. to 260° C., for example:

(i) cyclic silicones comprising 3 to 7 silicon atoms, for example, 4 to 5 silicon atoms. These cyclic silicones are, for example, octamethylcyclotetrasiloxane sold under the name Volatile Silicone 7207 by Union Carbide or Silbione 70045 V 2 by Rhodia Chimie, decamethylcyclopentasiloxane sold, for example, under the name Volatile Silicone 7158 by Union Carbide, and Silbione 70045 V 5 by Rhodia Chimie, and mixtures thereof.

Non-limiting mention may also be made of cyclocopolymers of the dimethylsiloxanes/methylalkylsiloxane type, such as Volatile Silicone FZ 3109 sold, for instance, by the company Union Carbide, having the chemical structure:

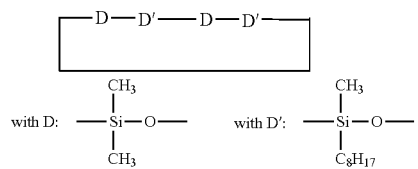

Non-limiting mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones comprising 2 to 9 silicon atoms and having a viscosity of less than or equal to $5\times10^{-6}$ m$^2$/s at 25° C., for example, decamethyltetrasiloxane sold under the name SH 200 by the company Toray Silicone. These silicones are also described in the article published in Cosmetics and Toiletries, Vol. 91, Jan. 76, pp. 27-32, Todd & Byers "Volatile Silicone Fluids for Cosmetics".

In at least one embodiment, non-limiting examples of non-volatile silicones that may be used in the present disclosure include polyalkylsiloxanes, polyarylsiloxanes, polyalkylarylsiloxanes, silicone gums, resins, polyorganosiloxanes modified with organofunctional groups, and mixtures thereof.

Non-limiting examples of non-volatile silicones include, but are not limited to polyalkylsiloxanes, for example, polydimethylsiloxanes comprising trimethylsilyl end with a viscosity ranging from $5\times10^{-6}$ to 2.5 m$^2$/s at 25° C., for instance, $1\times10^{-5}$ to 1 m$^2$/s. The viscosity of the silicones is measured, for example, at −25° C. according to ASTM standard 445 Appendix C.

Among these polyalkylsiloxanes, the following commercial products may be cited in a non-restrictive manner:
the Silbione oils of the 47 and 70 047 series or the Mirasil oils sold by Rhodia Chimie, for example, the oil 70 047 V 500 000;
the oils of the Mirasil series sold by the company Rhodia Chimie;
the oils of the 200 series from the company Dow Corning, such as, DC200 of viscosity of 60,000 cSt;
the Viscasil oils from General Electric and certain oils of the SF series (SF 96, SF 18) from General Electric.

Also useful herein are polydimethylsiloxanes comprising dimethylsilanol end groups (Dimethiconol according to the CTFA name) such as the oils of the 48 series from the company Rhodia Chimie.

Non-limiting mention may also be made among this class of polyalkylsiloxanes, for example, products sold under the names Abil Wax 9800 and 9801 by the company Goldschmidt, which are poly($C_1$-$C_{20}$)alkylsiloxanes.

The polyalkylarylsiloxanes that may be used in the present disclosure may, in at least one embodiment, be chosen from polydimethylmethylphenylsiloxanes and polydimethyldiphenylsiloxanes with a viscosity ranging from $1\times10^{-5}$ to $5\times10^{-2}$ m$^2$/s at 25° C.

Examples of such polyalkylarylsiloxanes include, but are not limited to:
the Silbione oils of the 70 641 series from Rhodia Chimie;
the oils of the Rhodorsil 70 633 and 763 series from Rhodia Chimie;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Silicone gums useful according to the present disclosure include, but are not limited to polydiorganosiloxanes with high number-average molecular masses ranging from 200,000 to 1,000,000, used alone or as a mixture in a solvent. Non-limiting examples of this solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, and mixtures thereof.

Polydiorganosiloxanes used in at least one embodiment of the present disclosure may include:
polydimethylsiloxane,
polydimethylsiloxane/methylvinylsiloxane gums,
polydimethylsiloxane/diphenylsiloxane,
polydimethylsiloxane/phenylmethylsiloxane,
polydimethylsiloxane/diphenylsiloxane/methylvinylsiloxane.

Products useful in at least one embodiment of the present disclosure are mixtures such as:
mixtures formed from a polydimethylsiloxane hydroxylated at the end of the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone such as the product SF 1214 Silicone Fluid from the company General Electric; this product is an SF 30 gum corresponding to a dimethicone, having a mean numerical molecular weight of 500,000, dissolved in the oil SF 1202 Silicone Fluid corresponding to decamethylcyclopentasiloxane;

mixtures of two PDMSs of different viscosities, for example, a PDMS gum and a PDMS oil, such as the product SF 1236 from the company General Electric. The product SF 1236 is a mixture of an SE 30 gum defined above, having a viscosity of 20 $m^2/s$, and an SF 96 oil of viscosity of $5 \times 10^{-6}$ $m^2/s$. This product may, for example, comprise 15% of SE 30 gum and 85% of an SF 96 oil.

Organopolysiloxane resins useful according to the present disclosure include, but are not limited to crosslinked siloxane systems comprising the following moieties:

$R_2SiO_{2/2}$, $R_3SiO_{1/2}$, $RSiO_{3/2}$ and $SiO_{4/2}$ wherein R is chosen from a $C_1$-$C_{16}$ hydrocarbon-based group and a phenyl group. Among these products are those wherein R is a $C_1$-$C_4$ lower alkyl radical, for example, methyl, or a phenyl radical.

Non-limiting mention may be made among these resins, for example, of the product sold under the name Dow Corning 593 or those sold under the names Silicone Fluid SS 4230 and SS 4267 by the company General Electric, which are silicones of dimethyl/trimethyl siloxane structure.

Other useful resins include, but are not limited to, the trimethyl siloxysilicate type resins sold, for instance, under the names X22-4914, X21-5034 and X21-5037 by the company Shin-Etsu.

The organomodified silicones that can be used in accordance with the present disclosure may be chosen from silicones as defined above and comprising in their structure at least one organofunctional group attached via a hydrocarbon-based radical.

Examples of organomodified silicones include, but are not limited to polyorganosiloxanes comprising:
polyethyleneoxy and/or polypropyleneoxy groups optionally comprising $C_6$-$C_{24}$ alkyl groups, such as the products known as dimethicone copolyol sold by the company Dow Corning under the name DC 1248 and the oils Silwet L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold, for example, under the name GP 4 Silicone Fluid and GP 7100 by the company Genesee, and the products sold, for instance, under the names Q2 8220 and Dow Corning 929 and 939 by the company Dow Corning. The substituted amine groups include, for example, $C_1$-$C_4$ aminoalkyl groups;

thiol groups such as the products sold, for instance, under the names GP 72 A and GP 71 from Genesee;

alkoxylated groups such as the product sold, for example, under the name Silicone Copolymer F-755 by SWS Silicones and Abil Wax 2428, 2434 and 2440 by the company Goldschmidt;

hydroxylated groups such as the polyorganosiloxanes comprising a hydroxyalkyl functional group, such as those described in French Patent Application No. 85/16334, chosen from those of formula (XI):

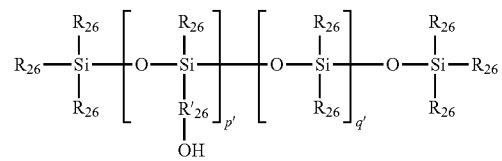

(XI)

wherein:
$R_{26}$, is chosen from methyl and phenyl radicals; wherein at least 60 mol % are methyl;

$R'_{26}$ is a $C_2$-$C_{18}$ divalent hydrocarbon-based alkylene chain unit;

p' is an integer or decimal ranging from 1 to 30;

q' is an integer or decimal ranging from 1 to 150;

acyloxyalkyl groups such as the polyorganosiloxanes described in U.S. Pat. No. 4,957,732 and chosen from those of formula (XII):

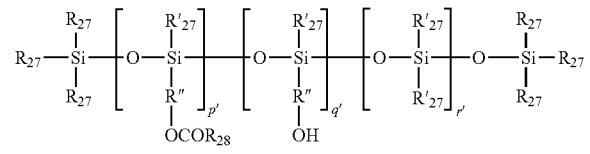

(XII)

wherein:
$R_{27}$ is chosen from methyl, phenyl, —$OCOR_{28}$ and a hydroxyl group, and in at least one embodiment, one of the radicals $R_{27}$ per silicon atom is OH;

$R'_{27}$ is chosen from methyl and phenyl, wherein at least 60 mol % of all the radicals $R_4$ and $R'_4$ are methyl;

$R_{28}$ is chosen from $C_8$-$C_{20}$ alkyl and alkenyl;

R" is chosen from $C_2$-$C_{18}$ linear and branched divalent hydrocarbon-based alkylene radicals;

r' is an integer or decimal ranging from 1 to 120;

p' is an integer or decimal ranging from 1 to 30;

q'is 0 or is less than 0.5 p', wherein p'+q' ranges from 1 to 30; the polyorganosiloxanes of formula (XII) may contain groups:

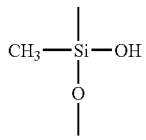

in an amount not exceeding 15% of the sum p+q+r;

anionic groups of carboxylic type, for example, in the products described in European Patent No. 186 507 from the company Chisso Corporation, and of alkylcarboxylic type, such as those present in the product X-22-3701 E from the company Shin-Etsu; 2-hydroxyalkyl sulfonate; 2-hydroxyalkyl thiosulfate such as the products sold by the company Goldschmidt under the names Abil S201 and Abil S255;

hydroxyacylamino groups, such as the polyorganosiloxanes described in European Patent Application No. 342 834 and the product Q2-8413 from the company Dow Corning.

Also useful herein are silicones comprising a polysiloxane portion and a portion comprising a non-silicone organic chain, wherein one of the two portions constitutes the main chain of the polymer and the other is grafted onto the main chain. These polymers are described, for example, in European Patent Application Nos. 412 704, 412 707, 640 105, 582 152, and in International Application Nos. WO 95/00578, and WO 93/23009 and in U.S. Pat. Nos. 4,693,935, 4,728,571 and 4,972,037. In at least one embodiment. these polymers are, for example, anionic or nonionic.

Also suitable for use in the present disclosure are polymers, for example, copolymers that can be obtained by free-radical polymerization starting with a monomer mixture comprising:

a) tert-butyl acrylate present in an amount ranging from 50% to 90% by weight;

b) acrylic acid present in an amount ranging from 0% to 40% by weight;

c) silicone macromer present in an amount ranging from 5% to 40% by weight of formula (XIII):

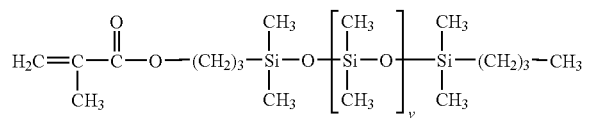

wherein v is an integer or decimal ranging from 5 to 700; wherein the weight percentages are calculated relative to the total weight of the monomers.

Also suitable for use in the present disclosure are grafted silicone polymers, for example, polydimethylsiloxanes (PDMS) onto which are grafted, via a connecting chain unit of thiopropylene type, mixed polymer units of poly(meth) acrylic acid type and of polyalkyl(meth)acrylate type and polydimethylsiloxanes (PDMS) onto which are grafted, via a connecting chain unit of thiopropylene type, polymer units of polyisobutyl(meth)acrylate type.

According to the present disclosure, the silicones disclosed herein may be used as such or in the form of emulsions, nanoemulsions or microemulsions.

According to at least one embodiment of the present disclosure, the polyorganosiloxanes that are suitable for use may include:

non-volatile silicones chosen from polyalkylsiloxanes comprising trimethylsilyl end groups, such as oils having a viscosity ranging from 0.2 m$^2$/s to 2.5 m$^2$/s at 25° C., such as the oils of the DC200 series from Dow Corning, for example, oils with a viscosity of 60,000 cSt, of the Silbione 70047 and 47 series and further for example, the oil 70 047 V 500 000, sold by the company Rhodia Chimie, polyalkylsiloxanes comprising dimethylsilanol end groups, such as dimethiconols, or polyalkylarylsiloxanes such as the oil Silbione 70641 V 200 sold, for instance, by the company Rhodia Chimie;

the organopolysiloxane resin sold, for example, under the name Dow Corning 593;

polysiloxanes comprising amine groups, such as amodimethicones or trimethylsilylamodimethicones.

In at least one embodiment, the cationic proteins or cationic protein hydrolysates are, for example, chemically modified polypeptides bearing quaternary ammonium groups at the end of the chain or grafted thereto. Their molecular mass can range, for example, from 1,500 to 10,000 and further for example, from 2,000 to 5,000. Examples of suitable cationic proteins or cationic protein hydrolysates include, but are not limited to:

collagen hydrolysates bearing triethylammonium groups, such as the products sold for instance, under the name Quat-Pro E by the company Maybrook and referred to in the CTFA dictionary as "Triethonium Hydrolyzed Collagen Ethosulfate";

collagen hydrolysates bearing trimethylammonium and trimethylstearylammonium chloride groups, sold, for example, under the name Quat-Pro S by the company Maybrook and referred to in the CTFA dictionary as "Steartrimonium Hydrolyzed Collagen";

animal protein hydrolysates bearing trimethylbenzylammonium groups such as the products sold, for instance, under the name Crotein BTA by the company Croda and referred to in the CTFA dictionary as "Benzyltrimonium hydrolyzed animal protein";

protein hydrolysates bearing, on the polypeptide chain, quaternary ammonium groups comprising at least one $C_1$-$C_{18}$ alkyl radical.

Examples of protein hydrolysates, sold by the company Croda, include, but are not limited to:

Croquat L wherein the quaternary ammonium groups comprise a $C_{12}$ alkyl group;

Croquat M wherein the quaternary ammonium groups comprise $C_{10}$-$C_{18}$ alkyl groups;

Croquat S wherein the quaternary ammonium groups comprise a $C_{18}$ alkyl group;

Crotein Q wherein the quaternary ammonium groups comprise at least one $C_1$-$C_{18}$ alkyl group.

Also useful herein are quaternized proteins or hydrolysates chosen from those of formula (XIV):

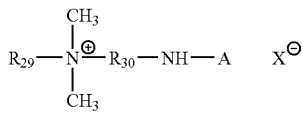
(XIV)

wherein:
- $X^-$ is chosen from an organic anion of an organic acid or an anion of a mineral acid;
- A is a protein residue derived from hydrolysates of collagen protein;
- $R_{29}$ is a lipophilic group comprising up to 30 carbon atoms; and
- $R_{30}$ is a $C_1$-$C_6$ alkylene group. Non-limiting mention may be made, for example, of the products sold by the company Inolex under the name Lexein QX 3000, referred to in the CTFA dictionary as "Cocotrimonium Collagen Hydrolysate".

Non-limiting mention may also be made of quaternized plant proteins such as wheat, corn or soybean proteins: as quaternized wheat proteins, or for example, quaternized plant proteins sold by the company Croda under the names Hydrotriticum WQ or QM, referred to in the CTFA dictionary as "Cocodimonium Hydrolysed Wheat Protein", Hydrotriticum QL, referred to in the CTFA dictionary as "Lauridimonium Hydrolysed Wheat Protein" or Hydrotriticum QS, referred to in the CTFA dictionary as "Steardimonium Hydrolysed Wheat Protein".

According to at least one embodiment of the present disclosure, the compounds of ceramide type are, for example, natural or synthetic ceramides, glycoceramides, pseudoceramides and neoceramides.

Non-limiting examples of compounds of ceramide type are described, for example, in German Patent Application Nos. 4 424 530, 4 424 533, 4 402 929, 4 420 736, International Patent Application Nos. WO 95/23807, WO 94/07844, WO 94/24097, WO 95/16665, WO 94/10131, European Patent Application Nos. 0 646 572, 0 227 994 and French Patent Application No. 2 673 179, the teachings of which are included herein by way of reference.

Compounds of ceramide type used in at least one embodiment of the present disclosure may include:
- 2-N-linoleoylaminooctadecane-1,3-diol,
- 2-N-oleoylaminooctadecane-1,3-diol,
- 2-N-palmitoylaminooctadecane-1,3-diol,
- 2-N-stearoylaminooctadecane-1,3-diol,
- 2-N-behenoylaminooctadecane-1,3-diol,
- 2-N-[2-hydroxypalmitoyl]aminooctadecane-1,3-diol,
- 2-N-stearoylaminooctadecane-1,3,4-triol, for example, N-stearoylphytosphingosine,
- 2-N-palmitoylaminohexadecane-1,3-diol,
- bis(N-hydroxyethyl-N-cetyl)malonamide,
- N-(2-hydroxyethyl)-N-(3-cetyloxy-2-hydroxypropyl) cetylamide,
- N-docosanoyl-N-methyl-D-glucamine, and mixtures thereof.

Cationic surfactants that may also be used herein, include: optionally polyoxyalkylenated primary, secondary and tertiary fatty amine salts, quaternary ammonium salts, imidazoline derivatives, and amine oxides of cationic nature.

Non-limiting examples of quaternary ammonium salts may include:
those of general formula (XV):

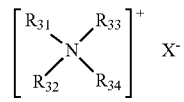
(XV)

wherein
- $R_{31}$ to $R_{34}$, which may be identical or different, are chosen from $C_1$-$C_{30}$ linear and branched aliphatic radicals and aromatic radicals such as aryl or alkylaryl. The aliphatic radicals may comprise heteroatoms such as oxygen, nitrogen, sulfur and halogens. The aliphatic radicals are chosen, for example, from alkyl, alkoxy, polyoxy($C_2$-$C_6$)alkylene, alkylamide, ($C_{12}$-$C_{22}$)alkylamido($C_2$-$C_6$) alkyl, ($C_{12}$-$C_{22}$)alkylacetate and hydroxyalkyl radicals, comprising from 1 to 30 carbon atoms;
- $X^-$ is an anion chosen from halides, phosphates, acetates, lactates, ($C_2$-$C_6$)alkyl sulfates, alkyl sulfonates and alkylaryl sulfonates;

quaternary ammonium salts of imidazolinium, such as, the salt of formula (XVI):

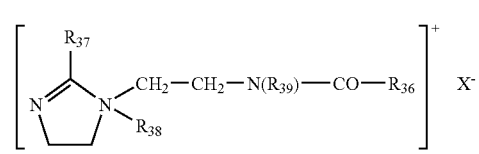
(XVI)

wherein
- $R_{36}$ may be chosen from a $C_8$-$C_{30}$ alkenyl and $C_8$-$C_{30}$ alkyl radicals, for example, tallow fatty acid derivatives;
- $R_{37}$ may be chosen from a hydrogen atom, $C_1$-$C_4$ alkyl radicals, $C_8$-$C_{30}$ alkenyl radicals and $C_8$-$C_{30}$ alkyl radicals;
- $R_{38}$ is a $C_1$-$C_4$ alkyl radical, for example, a methyl radical;
- $R_{39}$ is chosen from a hydrogen atom and $C_1$-$C_4$ alkyl radicals;
- $X^-$ is an anion chosen from halides, phosphates, acetates, lactates, alkyl sulfates, alkyl sulfonates and alkylaryl sulfonates;
- $R_{36}$ and $R_{37}$ may be chosen from a mixture of $C_{12}$-$C_{21}$ alkenyl and $C_{12}$-$C_{21}$, alkyl radicals, for example, tallow fatty acid derivatives.

A non-limiting example is the product sold, for example, under the name "Rewoquat W 75" by the company Degussa;

diquaternary ammonium salts of formula (XVII):

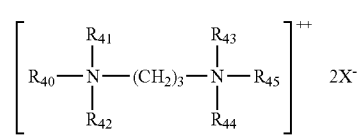
(XVII)

wherein:
- $R_{40}$ is a $C_{16}$-$C_{30}$ aliphatic radical;
- $R_{41}$, $R_{42}$, $R_{43}$, $R_{44}$ and $R_{45}$, which may be identical or different, are chosen from hydrogen or $C_1$-$C_4$ alkyl radicals; and X⁻ is an anion chosen from halides, acetates, phosphates, nitrates and methyl sulfates. A non-limiting example of diquaternary ammonium salts includes propane tallow diammonium dichloride;

According to at least one embodiment of the present disclosure, quaternary ammonium salts comprising at least one ester functional group that may be useful are, for example, those of formula (XVIII):

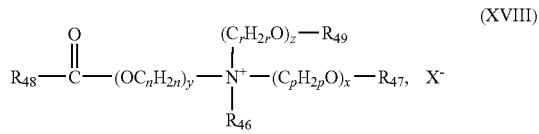

wherein
$R_{46}$ is chosen from $C_1$-$C_6$ alkyl radicals, $C_1$-$C_6$ hydroxyalkyl and dihydroxyalkyl radicals;
$R_{47}$ is chosen from:
a radical

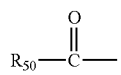

linear or branched, saturated or unsaturated $C_1$-$C_{22}$ hydrocarbon-based radicals $R_{51}$,
a hydrogen atom,
$R_{49}$ is chosen from:
a radical

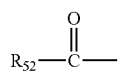

linear or branched, saturated or unsaturated $C_1$-$C_6$ hydrocarbon-based radicals $R_{53}$,
a hydrogen atom,
$R_{48}$, $R_{50}$ and $R_{52}$, which may be identical or different, are chosen from linear or branched, saturated or unsaturated $C_7$-$C_{21}$ hydrocarbon-based radicals;
n, p and r, which may be identical or different, are integers ranging from 2 to 6;
y is an integer ranging from 1 to 10;
x and z, which may be identical or different, are integers ranging from 0 to 10;
X⁻ is a simple or complex organic or inorganic anion; and
with the proviso that the sum x+y+z is from 1 to 15, that when x is 0, then $R_{47}$ is $R_{51}$ and that when z is 0, then $R_{49}$ is $R_{53}$.

The $R_{46}$ alkyl radicals may be linear or branched and in at least one embodiment, linear.

$R_{46}$ may be a methyl, ethyl, hydroxyethyl or dihydroxypropyl radical and in at least one embodiment, a methyl or ethyl radical.

In at least one embodiment, the sum x+y+z is for example, from 1 to 10.

When $R_{47}$ is a hydrocarbon-based radical $R_{51}$, it may be long and comprise 12 to 22 carbon atoms, or short and comprise 1 to 3 carbon atoms.

When $R_{49}$ is a hydrocarbon-based radical $R_{53}$, it comprises 1 to 3 carbon atoms.

$R_{48}$, $R_{50}$ and $R_{52}$, which may be identical or different, are chosen from linear or branched, saturated or unsaturated $C_{11}$-$C_{21}$ hydrocarbon-based radicals. In another embodiment $R_{48}$, $R_{50}$ and $R_{52}$ may be chosen from linear or branched, saturated or unsaturated, $C_{11}$-$C_{21}$ alkyl and alkenyl radicals.

In at least one embodiment, x and z, which may be identical or different, are 0 or 1.

In another embodiment, y is 1.

In at least one embodiment, n, p and r, which may be identical or different, are 2 or 3.

The anion is, in at least one embodiment, chosen from a halide, for example, chloride, bromide and iodide, and an alkyl sulfate, for example, methyl sulfate. In another embodiment, methanesulfonate, phosphate, nitrate, tosylate, an anion derived from an organic acid, such as acetate or lactate, or any other anion that is compatible with the ammonium containing an ester functional group, may be used.

The anion X⁻ is chosen, in at least one embodiment, from chloride or methyl sulfate.

In at least one embodiment, ammonium salts of formula (XVIII) may be used wherein
$R_{46}$ is a methyl or ethyl radical,
x and y are 1;
z is 0 or 1;
n, p and r are 2;
$R_{47}$ is chosen from:
a radical

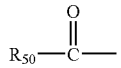

methyl, ethyl, $C_{14}$-$C_{22}$ hydrocarbon-based radicals;
and a hydrogen atom;
$R_{49}$ is chosen from:
a radical

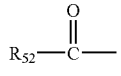

and a hydrogen atom;
$R_{48}$, $R_{50}$ and $R_{52}$, which may be identical or different, are chosen from linear or branched, saturated or unsaturated $C_{13}$-$C_{17}$ hydrocarbon-based radicals. In at least one embodiment, $R_{48}$, $R_{50}$ and $R_{52}$ are chosen from linear or branched, saturated or unsaturated $C_{13}$-$C_{17}$ alkyl and alkenyl radicals.

According to at least one embodiment, the hydrocarbon-based radicals are linear.

According to the present disclosure, the compounds of formula (XVI) may be chosen from, for example, diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts, for example, chloride or methyl sulfate, and mixtures thereof. The acyl radicals may comprise 14 to 18 carbon atoms and may be derived from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which may be oxyalkylenated, with fatty acids or with fatty acid mixtures of plant or animal origin, or by transesterification of the methyl esters thereof. This esterification is followed by a quaternization using an alkylating agent such as an alkyl halide, for example, methyl or ethyl halide, a dialkyl sulfate, for example, dimethyl or diethyl sulfate, methyl methanesulfonate, methyl para-toluenesulfonate, glycol chlorohydrin and glycerol chlorohydrin.

Such compounds are sold, for example, under the names Dehyquart by the company Cognis, Stepanquat by the company Stepan, Noxamium by the company CECA or Rewoquat WE 18 by the company Degussa.

The ammonium salts, which may comprise at least one ester functional group and may be used in the context of the present disclosure are further described in U.S. Pat. Nos. 4,874,554 and 4,137,180.

According to the present disclosure, non-limiting examples of quaternary ammonium salts of formula (XV) that may be used herein are chosen from tetraalkylammonium chlorides such as, dialkyldimethylammonium chlorides and alkyltrimethylammonium chlorides, wherein the alkyl radical comprises 12 to 22 carbon atoms, for example, behenyltrimethylammonium chloride, distearyidimethylammonium chloride, cetyltrimethylammonium chloride, and benzyldimethylstearylammonium chloride, or stearamidopropyldimethyl(myristyl acetate)ammonium chloride sold, for instance, under the name Ceraphyl 70 by the company Van Dyk.

The saturated fatty acids, in at least one embodiment, are chosen from myristic acid, palmitic acid, stearic acid, behenic acid and isostearic acid.

In a further embodiment, the fatty acid esters are chosen from carboxylic acid esters, for example, monocarboxylic esters, dicarboxylic esters, tricarboxylic esters and tetracarboxylic esters.

The monocarboxylic acid esters may, in at least one embodiment, be chosen from linear or branched, saturated or unsaturated, $C_1$-$C_{26}$ aliphatic acid monoesters of linear or branched, saturated or unsaturated, $C_1$-$C_{26}$ aliphatic alcohols, wherein the total carbon number of these esters is greater than or equal to 10.

Suitable monoesters include, by way of non-limiting example, dihydroabietyl behenate, octyldodecyl behenate, isocetyl behenate; cetyl lactate, $C_{12}$-$C_{15}$ alkyl lactate, isostearyl lactate, lauryl lactate, linoleyl lactate, oleyl lactate, (iso)stearyl octanoate, isocetyl octanoate, octyl octanoate, cetyl octanoate, decyl oleate, isocetyl isostearate, isocetyl laurate, isocetyl stearate, isodecyl octanoate, isodecyl oleate, isononyl isononanoate, isostearyl palmitate, methylacetyl ricinoleate, myristyl stearate, octyl isononanoate, 2-ethylhexyl isononate, octyl palmitate, octyl pelargonate, octyl stearate, octyldodecyl erucate, oleyl erucate, ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isostearyl neopentanoate, and isodecyl neopentanoate.

Other esters useful herein include, by way of non-limiting example, $C_4$-$C_{22}$ di- or tricarboxylic acid esters of $C_1$-$C_{22}$ alcohols and mono-, di- or tricarboxylic acid esters of $C_2$-$C_{26}$ di-, tri-, tetra- or pentahydroxy alcohols.

In at least one embodiment, non-limiting mention may also be made of diethyl sebacate, diisopropyl sebacate, adipate, di-n-propyl adipate, dioctyl adipate, diisostearyl adipate, dioctyl maleate, glyceryl undecylenate, octyldodecylstearoyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate dicaprate, tridecyl erucate, triisopropyl citrate, triisostearyl citrate, glyceryl trilactate, glyceryl trioctanoate, trioctyldodecyl citrate and trioleyl citrate.

Among the esters mentioned above, in at least one embodiment, the following non-limiting examples may be used herein: palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate, cetyl octanoate, isostearyl neopentanoate, and isodecyl neopentanoate.

The fluorinated oils are, for example, the perfluoropolyethers described in European Patent Application No. 486 135 and the fluorohydrocarbon compounds described in International Patent Application No. WO 93/11103, both of which are incorporated herein by way of reference.

As used herein, "fluorohydrocarbon compounds" is understood to mean compounds whose chemical structure comprises a carbon skeleton wherein certain hydrogen atoms have been replaced with fluorine atoms.

The fluorinated oils can also be fluorocarbons such as fluoroamines, for example, perfluorotributylamine, and fluorohydrocarbons, for example, perfluorodecahydro-naphthalene, fluoro esters and fluoro ethers.

The perfluoropolyethers are sold, for example, under the trade names Fomblin, by the company Montefluos and Krytox, by the company Du Pont.

Among the fluorohydrocarbon compounds that may be mentioned, are the esters of fluorine-containing fatty acids such as the product sold, for example, under the name Nofable FO by the company Nippon Oil.

The composition of the present disclosure may also comprise at least one mixture of conditioning agents.

Accordingly, the at least one conditioning agent may be present in an amount ranging from 0.001% to 20% by weight, for example, from 0.01% to 10% by weight and further for example, from 0.1% to 3% by weight, relative to the total weight of the final composition.

The cosmetically acceptable medium of the composition for wash-protecting the color of keratin fibers according to the disclosure may be in the form of aqueous or aqueous-alcoholic lotions, oils, gels, milks, creams, emulsions and in the form of a mousse.

The compositions for wash-protecting the color of keratin fibers according to the present disclosure may be packaged in various forms that include: vaporizers, pump-dispenser bottles and aerosol containers in order to apply the composition in vaporized form and in the form of a mousse. Such packaging forms are indicated, for example, when it is desired to obtain a spray, a lacquer or a mousse for treating the hair.

In at least one embodiment, the pH of the composition for wash-protecting the color of keratin fibers may range from 1 to 11, for example, from 2 to 6, and may be adjusted to the desired value by acidification or with basifying agents that are well known in the prior art for compositions applied to keratin fibers.

Non-limiting examples of basifying agents that may be included in the present disclosure are aqueous ammonia, alkali metal carbonates, alkanolamines such as monoethanolamine, diethanolamine and triethanolamine and also derivatives thereof, oxyethylenated hydroxyalkylamines and ethylenediamines, oxypropylenated hydroxyalkyl-amines and ethylenediamines, sodium hydroxide, potassium hydroxide and compounds having the formula below:

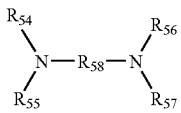

wherein:
$R_{58}$ is a propylene residue which may be substituted with a hydroxyl group or a $C_1$-$C_4$ alkyl radical;
$R_{54}$, $R_{55}$, $R_{56}$ and $R_{57}$, which may be identical or different, is chosen from a hydrogen atom, a $C_1$-$C_4$ alkyl radical or a $C_1$-$C_4$ hydroxyalkyl radical.

Non-limiting examples of acidifying agents that may be useful herein include, but are not limited to mineral and organic acids, for instance, hydrochloric acid, orthophosphoric acid, carboxylic acids, for instance, tartaric acid, citric acid, lactic acid, and sulfonic acids.

Also disclosed herein is a process for wash-protecting the color of artificially dyed keratin fibers, wherein the process comprises applying to the fibers, after dyeing, at least one zinc-based compound chosen from zinc-based mineral compounds and zinc-based non-nitrogenous organic compounds or at least one composition comprising, in a cosmetically acceptable medium, at least one zinc-based compound chosen from zinc-based mineral compounds and zinc-based non-nitrogenous organic compounds.

In at least one embodiment, the composition comprising the at least one zinc-based compound is applied to the fibers after the dyeing step, which may preceded or followed by a rinsing step and/or washing step with shampoo.

The process according to the disclosure, may additionally comprise a step of total or partial drying of the keratin fibers with a hairdryer. According to another embodiment of the present disclosure, the process for protecting the color of keratin fibers may comprise a step of heating the composition comprising the at least one zinc-based compound at a temperature less than or equal to 120° C., which will then be applied directly to the keratin fibers.

The process for wash-protecting the color of keratin fibers may also comprise a step of heating the keratin fibers during or after application of the composition comprising the at least one zinc-based compound.

The heating of the keratin fibers may be performed, for example, with an iron, a liquid water/steam mixture or by means of a heating hood.

The heating iron that may be useful in the context of the present disclosure is a heating iron conventionally used in the field of haircare, for example a crimping iron or a smoothing iron. Other non-limiting examples of irons useful herein are flat or round irons described in U.S. Pat. Nos. 4,103,145, 4,308,878, 5,983,903, 5,957,140 and 5,494,058. The iron may be applied by successive separate touches or for a time period of a few seconds, or by gradually moving or sliding it along the locks, or applying the iron to the keratin fibers after pausing after the application of the color-protecting composition. The pause will range, for example, from 30 seconds to 60 minutes, such as from 1 to 30 minutes. In at least one embodiment, the temperature ranges from 60° C. to 120° C.

The liquid water/steam mixture which may be used in accordance with the present disclosure may have a temperature of at least 35° C.

The liquid water/steam mixture may constitute a mist and may also comprise at least one other gas such as oxygen and nitrogen, and mixtures of gases such as air, and other vaporizable compounds.

In at least one embodiment, the temperature of the liquid water/steam mixture may be greater than or equal to 40° C., for example, it may range between 40° C. and 75° C.

In another embodiment, the liquid water/steam mixture may be placed in contact with the fiber for a time ranging from 1 second to 1 hour, for example, from 5 minutes to 15 minutes. The application of the mixture may be repeated several times on the same fiber, each operation being performed for a time as indicated above. In another embodiment, the composition comprising the at least one zinc-based compound is first applied to the hair and these locks are thus impregnated and then subjected to the action of the liquid water/steam mixture under the conditions mentioned above, and the locks are thus treated and then cooled, for example, by sending over or through them a stream of cold air or of air at ambient temperature.

The liquid water/steam mixture, used in accordance with the present disclosure, may be produced using any apparatus known in the art and intended for this purpose. According to the present disclosure, the liquid water/steam mixture is diffused onto the keratin fibers, for example, human hair, using an apparatus comprising at least one steam generator directly connected to a hood. A non-limiting example of this type of apparatus is that sold under the name Micromist® by the company Takara Belmont.

According to at least one embodiment of the present disclosure, the dyeing process comprises applying to human keratin fibers, for instance, hair, at least one dye composition (A) chosen from direct dye compositions and oxidation dye compositions, optionally in the presence of an oxidizing agent, for a time that is sufficient to develop the color, and then applying a composition (B) comprising, in a cosmetically acceptable medium, at least one zinc-based compound as defined above.

In at least one embodiment, the application of the composition (A) may be followed by rinsing and/or drying of the keratin fibers.

The application of the composition (B) may, in at least one embodiment, be followed by rinsing and/or drying of the keratin fibers. Composition (B) may be preheated under the same conditions defined above. The application of composition (B) may be followed by heating of the keratin fibers under the same conditions defined above.

In another embodiment, composition (B) may be applied after applying the at least one dye composition (A). Composition (B) comprising the at least one zinc-based compound may also be applied immediately after dyeing, or after a delay. As used herein, "after a delay" is understood to mean an application that takes place a few hours or one or several days, for example, from 1 to 15 days, after dyeing. In at least one embodiment, composition (B) will be applied immediately after dyeing the keratin fibers wherein the applications of the composition may be repeated between two colorations.

The nature and concentration of the at least one dye present in the at least one dye composition (A) may be chosen in accordance with the general knowledge in the art.

In the case of lightening direct dyeing operations, the dye compositions (A) result from the mixing, at the time of use, of a dye composition ($A_1$) comprising at least one direct dye and a composition ($A_2$) comprising an oxidizing agent.

In the case of oxidation dyeing, the dye compositions (A) result from the mixing, at the time of use, of a dye composition ($A_3$) comprising at least one oxidation base and optionally at least one coupler and/or a direct dye and of a composition ($A_4$) comprising an antioxidant.

The at least one direct dye may be chosen from compounds that absorb light radiation in the visible range (400-750 nm). They may further be chosen from nonionic, anionic and cationic direct dyes.

In at least one embodiment of the present disclosure, the at least one direct dye may be chosen from nitrobenzene dyes, azo dyes, anthraquinone dyes, naphthoquinone dyes, benzoquinone dyes, phenothiazine dyes, indigoid dyes, xanthene-dyes, phenanthridine dyes, phthalocyanin dyes, triarylmethane-based dyes, and mixtures thereof.

Non-limiting examples of nitrobenzene dyes may include red and orange compounds, for example, 1-hydroxy-3-nitro-4-N-(γ-hydroxypropyl)aminobenzene, N-(β-hydroxyethyl) amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)amino-benzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)-amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine, 1-amino-2-nitro-4-hydroxy-5-methylbenzene, and mixtures thereof.

The nitrobenzene direct dyes may also be chosen from yellow dyes and green-yellow dyes, for instance, 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoro-methylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene and 4-(β-hydroxyethyl) amino-3-nitrobenzamide.

Blue and violet nitrobenzene dyes that may be useful to the present disclosure include: 1-(β-hydroxyethyl)amino-4-N, N-bis(β-hydroxyethyl)amino-2-nitrobenzene, 1-(γ-hydroxypropyl)amino-4-N,N-bis(β-hydroxyethyl)amino-2-nitrobenzene, 1-(β-hydroxyethyl)amino-4-(N-methyl, N-β-hydroxyethyl)amino-2-nitrobenzene, 1-(β-hydroxyethyl) amino-4-(N-ethyl, N-β-hydroxyethyl)amino-2-nitrobenzene, 1-(β,γ-dihydroxypropyl)amino-4-(N-ethyl, N-β-hydroxyethyl)amino-2-nitrobenzene, and 2-nitro-para-phenylenediamines of the following formula:

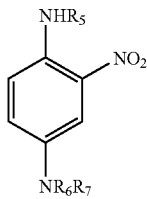

wherein:
R$_6$ is chosen from a C$_1$-C$_4$ alkyl radical, a β-hydroxyethyl radical, a β-hydroxypropyl radical and a γ-hydroxypropyl radical;
R$_5$ and R$_7$, which may be identical or different, are chosen from β-hydroxyethyl radicals, β-hydroxypropyl radicals, γ-hydroxypropyl radicals and β,γ-dihydroxypropyl radicals, wherein at least one of the radicals R$_6$, R$_7$ or R$_5$ is a γ-hydroxypropyl radical and R$_6$ and R$_7$ are not simultaneously a β-hydroxyethyl radical when R$_6$ is a γ-hydroxypropyl radical, such as those described in French Patent No. 2 692 572.

It is understood that azo dyes are compounds comprising in their structure at least one —N=N— sequence not included in a ring; methine dyes are compounds comprising in their structure at least one —C=C— sequence not included in a ring; and azomethine dyes are compounds comprising in their structure at least one —C=N— sequence not included in a ring.

In at least one embodiment, the triarylmethane-based dyes comprise in their structure at least one compound chosen from those of the following formula:

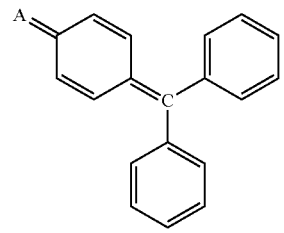

wherein A is chosen from an oxygen and nitrogen atom.

In another embodiment, the xanthene dyes may comprise in their structure at least one sequence of formula:

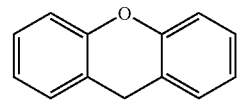

In yet another embodiment, the phenanthridine dyes may comprise in their structure at least one sequence of formula:

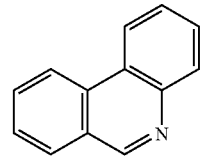

In at least another embodiment, the phthalocyanin dyes may comprise in their structure at least one sequence of formula:

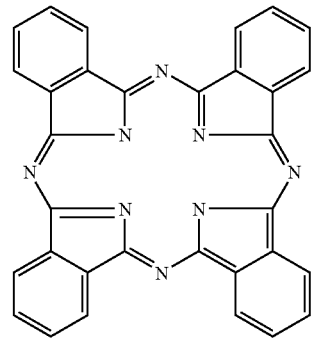

In another embodiment, the phenothiazine dyes may comprise in their structure at least one sequence below:

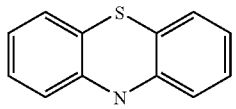

The direct dyes may also be chosen from basic dyes such as those listed in the Color Index, 3rd edition, for example, those under the names Basic Brown 16, Basic Brown 17, Basic Yellow 57, Basic Red 76, Basic Violet 10, Basic Blue 26 and Basic Blue 99; acidic direct dyes listed in the Color Index, 3rd edition, under the names Acid Orange 7, Acid Orange 24, Acid Yellow 36, Acid Red 33, Acid Red 184, Acid Black 2, Acid Violet 43, and Acid Blue 62, and cationic direct dyes such as those described in International Patent Application Nos. WO 95/01772, WO 95/15144 and European Patent Application No. 714 954, the contents of which are incorporated herein in their entireties, for example, Basic Red 51, Basic Orange 31, and Basic Yellow 87.

According to at least one embodiment, the at least one direct dye may be present in the composition in an amount ranging from 0.0005% to 12% by weight, for example, ranging from 0.005% to 6% by weight relative to the total weight of the composition.

The oxidation bases may be chosen from oxidation bases conventionally used in oxidation dyeing, for example, para-phenylenediamines, bis(phenyl)alkylene-diamines, para-aminophenols, ortho-aminophenols and heterocyclic bases.

Non-limiting examples of para-phenylenediamines useful herein are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, N,N-diethyl-4-amino-3-methylaniline, N,N-bis(β-hydroxyethyl)-para-phenylenediamine, 4-N,N-bis(β-hydroxyethyl)amino-2-methylaniline, 4-N,N-bis(β-hydroxy-ethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetyl-aminoethyloxy-para-phenylenediamine and N-(β-methoxyethyl)-para-phenylenediamine, and acid addition salts thereof. In at least one embodiment, the para-phenylenediamines may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof. Non-limiting examples of the bis(phenyl)alkylenediamines include N,N'-bis(β-hydroxyethyl)-N,N'-bis(4'-aminophenyl)-1,3-diaminopropanol, N N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the acid addition salts thereof.

Suitable para-aminophenols may be chosen, by way of non-limiting example, from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Suitable ortho-aminophenols include, but are not limited to 2-aminophenol, 2-amino-5-methylphenol, 2-amino-6-methylphenol and 5-acetamido-2-aminophenol, and the acid addition salts thereof.

Suitable heterocyclic bases include, by way of non-limiting example, pyridine derivatives, pyrimidine derivatives, and pyrazole derivatives.

Non-limiting examples of pyridine derivatives include the compounds described, for example, in British Patent Nos. 1 026 978 and 1 153 196, such as 2,5-di-aminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diamino-pyridine, and the acid addition salts thereof.

Suitable pyrimidine derivatives include, by way of non-limiting example, the compounds described, for example, in German Patent No. 2 359 399; Japanese Patent Nos. 88-169 571 and 05-163 124; European Patent No. 0 770 375, and International Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. 2 750 048 such as pyrazolo[1,5-a]-pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-amino-pyrazolo[1,5-a]pyrimidin-7-ol; 3-aminopyrazolo[1,5-a]pyrimidin-5-ol; 2-(3-amino-pyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof and the tautomeric forms thereof, when a tautomeric equilibrium exists.

Suitable pyrazole derivatives may include, but are not limited to compounds described in German Patent Nos. 3 843 892, 4 133 957, 195 43 988, International Patent Application Nos. WO 94/08969, WO 94/08970 and French Patent Application No. 2 733 749, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenyl-pyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-tri-aminopyrazole, 3,5-diamino-1-methyl-4-methylaminopyrazole and 3,5-diamino-4-(β-hydroxyethyl) amino-1-methylpyrazole, and the acid addition salts thereof. When present, the at least one oxidation base may be present in the composition in an amount ranging from 0.0005% to 12% by weight, for example, ranging from 0.005% to 6% by weight relative to the total weight of the dye composition.

The dye compositions in accordance with the present disclosure may also comprise at least one coupler and/or at least one direct dye, to modify the shades and/or to enrich them with tints.

Non-limiting examples of couplers that may be used in the dye composition include meta-phenylenediamines, meta-aminophenols, meta-diphenols, naphthols and heterocyclic couplers, for instance, indole derivatives, indoline derivatives, pyridine derivatives, indazole derivatives, pyrazolo[1,5-b]-1,2,4-triazole derivatives, pyrazolo[3,2-c]-1,2,4-triazole derivatives, benzimidazole derivatives, benzothiazole derivatives, benzoxazole derivatives, 1,3-benzodioxole derivatives, pyrazolones, and the acid addition salts thereof.

In at least one embodiment, the at least one coupler may be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methyl-indole, 6-hydroxyindoline, 6-hydroxybenzomorpholine, 3,5-diamino-2,6-dimethoxypyridine, 1-N(β-hydroxyethyl)amino-3,4-methylenedioxybenzene, 2,6-bis(β-hydroxy-ethyleneamino)toluene, 2,6-dihydroxy-4-methylpyridine, 1H-3-methylpyrazol-5-one, 1-phenyl-3-methylpyrazol-5-one, and the acid addition salts thereof.

When present, the at least one coupler may be present in the composition in an amount ranging from 0.0001% to 10% by weight, for example, from 0.005% to 5% by weight relative to the total weight of the dye composition.

The dye composition in accordance with the present disclosure may also contain at least one adjuvant conventionally used in hair dye compositions, such as anionic, cationic, nonionic, amphoteric, zwitterionic surfactants, and mixtures thereof, anionic, cationic, nonionic, amphoteric, zwitterionic polymers and mixtures thereof, mineral or organic thickeners, antioxidants, penetrants, sequestrants, fragrances, buffers, dispersants, conditioning agents, for instance, silicones, film-forming agents, preserving agents and opacifiers.

It is to be understood that a person skilled in the art will take care to select the at least one optional additional compound such that the beneficial properties intrinsically associated with the oxidation dye composition in accordance with the present disclosure are not, or are not substantially, adversely affected by the envisaged addition.

The dye composition according to the present disclosure may be in various forms, such as liquids, creams and gels, or in any other form that is suitable for dyeing keratin fibers, for example, human hair.

The at least one oxidizing agent used in the lightening direct dyeing operation (direct dyeing with an oxidizing agent) or in the oxidation dyeing operation may be chosen in accordance with the general knowledge in the art.

In at least one embodiment of the present disclosure, the oxidizing agent may be chosen from hydrogen peroxide, urea peroxide, alkali metal bromates or ferricyanides, and persalts such as perborates and persulfates. Redox enzyme(s) such as laccases, peroxidases and two-electron oxidoreductases (such as uricase) may also be used, where appropriate in the presence of the respective donor or cofactor thereof.

According to at least one embodiment, the process may be used on hair that has been sensitized by hair treatments other than those mentioned in the present disclosure.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

EXAMPLE

Dyeing Step

At the time of use, a support oxidation dye composition, Majirouge® 6.66, was mixed weight-for-weight with aqueous hydrogen peroxide solution (L'Oréal Professional 20-volumes 6% aqueous hydrogen peroxide solution).

The mixture was then applied to locks of permanent-waved hair comprising 90% white hairs, at a rate of 10 g of dye mixture/g of lock. The leave-on time was 30 minutes on each side of the lock. The locks were then rinsed with water, and then washed with DOP Camomile shampoo and dried.

a) Protective Treatment Step:

An aqueous lotion comprising 1% by weight of AM (active material) of the zinc salts below:

| Applied treatment | Lock |
|---|---|
| Zinc chloride sold under the reference 21127-3 by Sigma Aldrich | A |
| Zinc sulfate sold under the reference 108881 by Merck | B |
| Zinc gluconate sold under the trade name Givobio G Zn 2 by Sigma SEPPIC | C | was then applied to the entire length of a dyed lock, at a rate of 2 grams per gram of hair.

The treated locks were then left to stand under a hood for 10 minutes.

The treated locks were then shampooed with DOP Camomile® shampoo.

Untreated locks (references) were also shampooed accordingly. The locks were then dried under a hood for 10 minutes at 60° C.

b) Steps of Color Fastness after Shampoo Washing:

The treated locks were then compared with untreated dyed locks in a shampoo wash-fastness test.

Accordingly, the locks were shampooed six times successively with DOP Camomile® shampoo, with intermediate drying.

Evaluation of the Colour Protection:

After the wash-fastness test of the treated and untreated locks, the degradation of the color was evaluated relative to dyed locks that had not undergone this test.

The evaluations were accompanied by spectrocolorimetric monitoring. Measurements were taken using a Minolta CM 2022 spectrocolorimeter.

The degradation caused by the wash-fastness test was thus expressed as $\Delta E$ $$\Delta E(\text{after test}-\text{before test}) = \sqrt{(\Delta L^{*2} + \Delta a^{*2} + \Delta b^{*2})}$$

The protection was then expressed as a difference in $\Delta E$ between the treated and untreated locks (positive difference=gain in color protection, negative difference=loss of protection).

Results:

After exposure to the wash-fastness test, substantial degradation of the color of the untreated dyed locks was observed (loss of $\Delta E=7.50$).

It was observed, surprisingly, that after this same test, the locks that have been treated with the zinc salts of the present disclosure showed significant protection of the color compared with the untreated locks.

These results were confirmed by the colorimetric measurements, which indicated a significant gain in $\Delta E$ relative to the untreated dyed locks.

Results of colour degradation after wash-fastness test (6 washes with DOP Camomile® shampoo):

| Lock | $\Delta E$ relative to locks not subjected to the fastness test | Gain as difference in $\Delta E$ relative to the washed control |
|---|---|---|
| Control (untreated locks) | 7.50 | — |
| Treatment A | 4.73 | 2.77 |
| Treatment B | 4.78 | 2.72 |
| Treatment C | 2.06 | 5.44 |

What is claimed is:

1. A cosmetic process for wash-protecting the color of artificially dyed keratin fibers, comprising
applying to the artificially dyed keratin fibers at least one zinc-based compound chosen from zinc sulfate, zinc chloride, zinc lactate, zinc gluconate, zinc phenolsufonate and zinc salicylate and derivatives thereof.

2. A process according to claim 1, wherein the artificially dyed keratin fibers are human keratin fibers.

3. A process according to claim 1, wherein the artificially dyed keratin fibers are dyed by oxidation dyeing in the presence of an oxidizing agent.

4. A process for wash-protecting the color of artificially dyed keratin fibers, comprising
applying to the artificially dyed fibers a composition comprising, in a cosmetically acceptable medium, at least one zinc-based compound chosen from zinc sulfate, zinc chloride, zinc lactate, zinc gluconate, zinc phenolsufonate and zinc salicylate and derivatives thereof.

5. A process according to claim 4, wherein the cosmetically acceptable medium for the composition comprises water or a mixture of water and of at least one cosmetically acceptable organic solvent.

6. A process according to claim 5, wherein the at least one organic solvent is chosen from $C_1$-$C_4$ lower alkanols.

7. A process according to claim 5, wherein the at least one solvent is present in the composition in an amount ranging from 1% to 40% by weight relative to the total weight of the composition.

8. A process according to claim 4, wherein the at least one zinc-based compound is present in an amount ranging from 0.005% to 30% by weight relative to the total weight of the composition.

9. A process according to claim 4, wherein the composition comprises at least one additive chosen from anionic, cationic, nonionic, amphoteric and zwitterionic surfactants; anionic, cationic, nonionic, amphoteric and zwitterionic polymers; mineral, organic, anionic, cationic, nonionic and amphoteric polymeric associative thickeners; penetrants; sequestrants; fragrances; buffers; dispersants; conditioning agents; volatile and non-volatile silicones; film-forming agents; ceramides; preserving agents; and opacifiers.

10. A process according to claim 4, wherein the composition is in a form chosen from an aqueous lotion, an aqueous-alcoholic lotion, an oil, a gel, a milk, a cream, an emulsion or a mousse.

11. A process according to claim 4, wherein the composition is packaged in a vaporizer, in a pump-dispenser bottle or in an aerosol container.

12. A process according to claim 4 wherein the pH of the composition comprising the at least one zinc-based compound ranges from 1 to 11.

13. A process according to claim 4, comprising an additional rinsing step and/or a washing step with shampoo before or after applying the composition comprising the at least one zinc-based compound.

14. A process according to claim 4, comprising an additional step of total or partial drying of the keratin fibers with a hairdryer.

15. A process according to claim 4, further comprising heating the composition comprising the at least one zinc-based compound, before applying the composition directly to the previously dyed keratin fibers.

16. A process according to claim 4, further comprising heating the keratin fibers, either during or after applying the composition comprising the at least one zinc-based compound.

17. A process for dyeing keratin fibers, comprising
applying to the keratin fibers at least one dye composition (A) chosen from direct dye compositions and oxidation dye compositions, optionally in the presence of at least one oxidizing agent and/or at least one coupler, wherein the dye composition is left for a period of time that is sufficient to develop the color; and
applying to the dyed keratin fibers a composition (B) comprising, in a cosmetically acceptable medium, at least one zinc-based compound chosen from zinc sulfate, zinc chloride, zinc lactate, zinc gluconate, zinc phenolsufonate and zinc salicylate and derivatives thereof.

18. A process according to claim 16, further comprising rinsing and/or drying the keratin fibers after applying composition (A).

19. A process according to claim 17, further comprising rinsing and/or drying and/or by heating the keratin fibers after applying composition (B).

20. A process according to claim 17, wherein composition (B) is preheated.

21. A process according to claim 17, wherein the dye composition (A) results from the mixing, at the time of use, of a dye composition ($A_1$) comprising at least one direct dye, and of a composition ($A_2$) comprising at least one oxidizing agent.

22. A process according to claim 17 wherein the dye composition (A) results from the mixing, at the time of use, of a dye composition ($A_3$) comprising at least one oxidation base and optionally at least one coupler and/or one direct dye, and of a composition ($A_4$) comprising at least one oxidizing agent.

* * * * *